US012582636B2

(12) United States Patent
Kim et al.

(10) Patent No.: US 12,582,636 B2
(45) Date of Patent: Mar. 24, 2026

(54) PHARMACEUTICAL COMPOSITE FORMULATION COMPRISING PROTON PUMP INHIBITOR AND ANTACID

(71) Applicant: HANMI PHARM. CO., LTD., Hwaseong-si (KR)

(72) Inventors: Bo Sik Kim, Seoul (KR); Hyuk Jun Cho, Uiwang-si (KR); Ho Taek Im, Paju-si (KR); Yong Il Kim, Gwacheon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 867 days.

(21) Appl. No.: 17/794,178

(22) PCT Filed: Jan. 22, 2021

(86) PCT No.: PCT/KR2021/000890
§ 371 (c)(1),
(2) Date: Jul. 20, 2022

(87) PCT Pub. No.: WO2021/150050
PCT Pub. Date: Jul. 29, 2021

(65) Prior Publication Data
US 2023/0058432 A1 Feb. 23, 2023

(30) Foreign Application Priority Data

Jan. 23, 2020 (KR) ........................ 10-2020-0009289
Jan. 22, 2021 (KR) ........................ 10-2021-0009234

(51) Int. Cl.
*A61K 31/4439* (2006.01)
*A61K 9/24* (2006.01)
*A61K 33/08* (2006.01)
*A61K 47/38* (2006.01)
*A61K 47/58* (2017.01)

(52) U.S. Cl.
CPC .......... *A61K 31/4439* (2013.01); *A61K 9/209* (2013.01); *A61K 33/08* (2013.01); *A61K 47/38* (2013.01); *A61K 47/58* (2017.08)

(58) Field of Classification Search
CPC .................................................... A61K 9/209
See application file for complete search history.

(56) References Cited

U.S. PATENT DOCUMENTS

| | | | | |
|---|---|---|---|---|
| 6,183,776 B1 * | 2/2001 | Depui | .................... | A61K 9/209 |
| | | | | 424/468 |
| 9,040,564 B2 | 5/2015 | Ukai et al. | | |
| 2003/0191159 A1 | 10/2003 | Phillips | | |
| 2004/0166162 A1 | 8/2004 | Niecestro et al. | | |
| 2004/0248939 A1 | 12/2004 | Sugaya et al. | | |
| 2005/0031696 A1 * | 2/2005 | Kolhe | .................. | A61K 9/2846 |
| | | | | 424/488 |
| 2008/0003281 A1 * | 1/2008 | Clemmensen | ............ | A61P 1/00 |
| | | | | 424/458 |
| 2009/0104264 A1 | 4/2009 | Bando et al. | | |
| 2011/0177164 A1 * | 7/2011 | Rajan | ................... | A61K 9/5078 |
| | | | | 427/2.21 |
| 2018/0177731 A1 * | 6/2018 | Choi | ......................... | A61P 1/04 |
| 2021/0030687 A1 | 2/2021 | Choi et al. | | |

FOREIGN PATENT DOCUMENTS

| | | |
|---|---|---|
| CN | 101259108 A | 9/2008 |
| EP | 0 813 424 B1 | 11/2002 |
| KR | 10-2008-0005575 A | 1/2008 |
| KR | 10-2013-0115593 A | 10/2013 |
| KR | 10-2017-0136771 A | 12/2017 |
| KR | 10-1849125 B1 | 4/2018 |
| KR | 10-2006777 B1 | 10/2019 |
| RU | 2 467 740 C2 | 11/2012 |
| WO | 2008/110070 A1 | 9/2008 |
| WO | 2011/144975 A1 | 11/2011 |

OTHER PUBLICATIONS

Office Action issued Jun. 7, 2024 in Russian Application No. 2022118961/04.
Klaus Kümmerer, "Pharmaceuticals in the Environment", Annu. Rev. Environ. Resour., 2010, vol. 35, pp. 57-75 (22 pages total).
Kondratieva T.S. et al., "Technology of dosage forms: Textbook in 2 volumes", vol. 1.—M.: Medicine, 1991, No. 496, pp. 36-39, pp. 72-73 (4 pages total).
I.M. Pertsev, "Pharmaceutical and medical-biological aspects of drugs", v.1, 1999, pp. 253-254 (4 pages total).
I. E. Smekhova et al., "Disintegrants and their influence on the dissolution of substances of biopharmaceutical classification system classes", Development and registration of medicines, 2018, vol. 4, N. 25, pp. 62-72 (11 pages total).
Sunethra K. Gunatilake, et al., "Effects of Binder on the Physico-chemical Properties and the Quality of Paracetamol Tablets", Der Pharma Chemica, 2016, vol. 8, No. 4, pp. 237-242 (6 pages total).
Extended European Search Report dated Jan. 3, 2024 issued by the European Patent Office in European Application No. 21744262.3.
Office Action dated Aug. 16, 2022 from the Korean Intellectual Property Office in KR Application No. 10-2021-009234.
International Search Report for PCT/KR2021/000890 dated May 7, 2021 [PCT/ISA/210].
Communication dated Nov. 18, 2025 issued by the Instituto Mexicano De La Propiedad Industrial in application No. MX/a/2022/009121.
Jose Eduardo Hernandez-Torres, et al., "Principales superdisgregantes sinteticos, mecanismos y factores que influyen en su actividad", Rev. Colomb. Cienc. Quim. Farm., vol. 43, No. 2, 2014, pp. 234-247 (15 pages total).

* cited by examiner

*Primary Examiner* — Gina C Justice
(74) *Attorney, Agent, or Firm* — Sughrue Mion, PLLC

(57) ABSTRACT

An aspect provides a pharmaceutical composite formulation containing: a first layer comprising a proton pump inhibitor or a pharmaceutically acceptable salt thereof as an active ingredient, a disintegrant, and a binder; and a second layer comprising, as an active ingredient, an antacid selected from magnesium hydroxide, magnesium oxide, or a mixture thereof.

7 Claims, 5 Drawing Sheets

| Control | MCC | HPC-L | Mg(OH)₂ |
|---|---|---|---|
| | | | |
| CrosCMC Na (Primellose) | CrosCMC Na (Acdisol) | Crospovidone (XL-10) | Crospovidone (Kollidon CL) |
| | | | |

EtOH

| EXAMPLE 2 | EXAMPLE 4 | COMPARATIVE EXAMPLE 3 |

PHARMACEUTICAL COMPOSITE FORMULATION COMPRISING PROTON PUMP INHIBITOR AND ANTACID

CROSS REFERENCE TO RELATED APPLICATIONS

This application is a National Stage of International Application No. PCT/KR2021/000890 filed Jan. 22, 2021, claiming priority based on Korean Patent Application Nos. 10-2020-0009289 filed Jan. 23, 2020 and 10-2021-0009234 filed Jan. 22, 2021.

TECHNICAL FIELD

The present disclosure relates to a pharmaceutical composite formulation including a proton pump inhibitor and an antacid, and more particularly, to a composite formulation having improved stability and an improved dissolution rate.

BACKGROUND ART

Gastroesophageal diseases such as peptic ulcer and gastroesophageal reflux disease occur when the attacking factor prevails over the defensive factor of the mucosa in the esophagus, stomach, and duodenum, and rapid gastric acid suppression is needed to protect digestive tract diseases from gastric acid attack.

Proton pump inhibitors (PPIs) inhibit a proton pump (H+/K+-ATPase) in the parietal cells, and are drugs that suppress the production of hydrochloric acid and weaken the acidity in the digestive system. The drug exhibits its medicinal effect on indigestion, gastroesophageal reflux disease, pharyngeal reflux disease, or peptic ulcer disease. In particular, a benzimidazole-based compound or a salt thereof is used as a treatment for peptic ulcer that has a proton pump inhibitory action, and examples thereof include omeprazole, lansoprazole, rabeprazole, pantoprazole, and esomeprazole.

However, such proton pump inhibitors have a problem in that they easily decompose or deform under acidic conditions. For example, esomeprazole readily decomposes in acid and is affected by moisture, heat, organic solvents, and light. Accordingly, the formulation stability and dissolution rate of the drug may easily decrease. In order to prevent this, a method of stabilizing the formulation by adding several excipients or coating an enteric polymer may be considered, but the compatibility of the proton pump inhibitor and the excipients included in the composite formulation is poor, the formulation stability is poor, or the expression of drug efficacy is delayed. For example, Korean Patent Publication No. 10-2008-0005575 proposes a method of stabilizing by coating an enteric polymer to improve the stability of a benzimidazole-based proton pump inhibitor, but when a drug is prepared using this method, a relatively large amount of an enteric polymer or an excess of additives is required, decomposition of the drug may not be prevented due to the easy exposure to gastric acid when the enteric coating layer is lost, and the time for onset of drug action is delayed.

Therefore, there is a need to develop a formulation capable of improving compatibility with excipients in a composite formulation, improving stability and dissolution rate of a proton pump inhibitor in a gastric acid environment, and providing rapid onset of drug action.

DESCRIPTION OF EMBODIMENTS

Technical Problem

An embodiment of the present disclosure provides a pharmaceutical composite formulation including a proton pump inhibitor or a pharmaceutically acceptable salt thereof, the composite formulation having improved stability and dissolution rate.

Solution to Problem

According to an aspect of one or more embodiments, a pharmaceutical composite formulation comprises: a first layer comprising a proton pump inhibitor or a pharmaceutically acceptable salt thereof as an active ingredient, a disintegrant, and a binder; and a second layer comprising, as an active ingredient, an antacid selected from magnesium hydroxide, magnesium oxide, or a mixture thereof.

Specific solutions to the problems are as follows.

(1) A pharmaceutical composite formulation comprising a first layer comprising a proton pump inhibitor or a pharmaceutically acceptable salt thereof as an active ingredient, a disintegrant, and a binder; and a second layer comprising, as an active ingredient, an antacid selected from magnesium hydroxide, magnesium oxide, or a mixture thereof.

(2) The proton pump inhibitor is one selected from the group consisting of esomeprazole, omeprazole, lansoprazole, rabeprazole, pantoprazole, and a mixture thereof.

(3) The disintegrant is one selected from the group consisting of crospovidone, sodium starch glycolate, and a mixture thereof.

(4) The binder is one selected from the group consisting of hydroxypropyl cellulose, hypromellose, polyvinylpyrrolidone, and a mixture thereof.

(5) An amount of the disintegrant is in a range of about 0.5 wt % to about 5.5 wt % based on the total weight of the first layer.

(6) An amount of the binder is in a range of about 5 wt % to about 15 wt % based on the total weight of the first layer.

(7) An amount of the binder is in a range of about 1.5 parts to about 4.5 parts by weight based on 1 part by weight of the disintegrant included in the first layer.

(8) An amount of the disintegrant is in a range of about 0.9 wt % to about 5 wt % based on the total weight of the first layer, and an amount of the binder is in a range of about 1.9 parts to about 4.5 parts by weight based on 1 part by weight of the disintegrant included in the first layer.

(9) An amount of the disintegrant is in a range of about 0.95 wt % to about 5 wt % based on the total weight of the first layer, and an amount of the binder is in a range of about 5 wt % to about 15 wt % based on the total weight of the first layer.

(10) The composite formulation is a double-layer tablet.

(11) When a test is conducted in a mixture solution including 75 mL of 0.1 N HCl and 225 mL of purified water at about 75±2 revolutions per minute (rpm) at a temperature of 37±0.5° C. according to the second method (paddle method) of the dissolution test of the United States Pharmacopeia (USP), the composite formulation simultaneously has, for 10 minutes, a dissolution rate of the proton pump inhibitor in a range of about 10% to about 50% and a dissolution rate of the antacid of about 70% or higher.

(12) The composite formulation simultaneously has, for 5 minutes, a dissolution rate of the proton pump inhibitor in a range of about 5% to about 30% and a dissolution rate of the antacid of about 60% or higher.

Advantageous Effects of Disclosure

A pharmaceutical composite formulation according to an embodiment may have improved stability and dissolution rate, does not have discoloration during long-term storage as the property stability is improved, and may reduce the total amount of related substances generated during the storage, thereby improving the quality of the product. Also, the composite formulation may release the proton pump inhibitor and the antacid with a time difference for each layer, and thus has an excellent effect of preventing acid degradation of the proton pump inhibitor even in a low pH environment of gastric juice in the body. In addition, the composite formulation may provide a fast-acting proton pump inhibitor by improving the dissolution rate of the proton pump inhibitor.

MODE OF DISCLOSURE

Figures 1A, 1B:
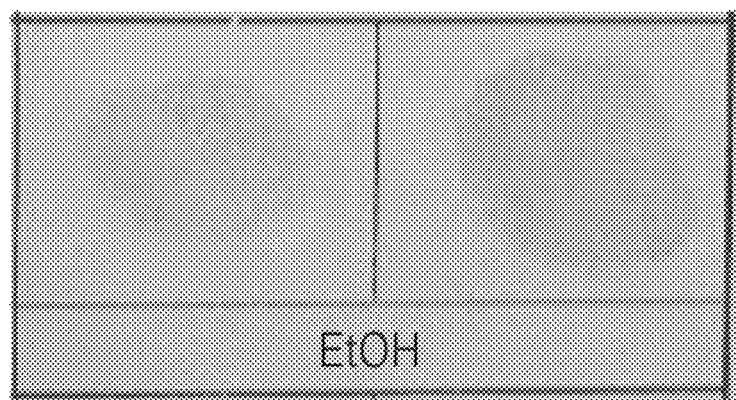
FIG. 1A shows changes in properties according to compatibility of excipient components included together with esomeprazole in a tablet.
FIG. 1B shows changes in properties according to compatibility of esomeprazole and ethanol.

Hereinafter, the present disclosure will be described in further detail.

Unless otherwise defined, all technical terms used herein have the same meaning as commonly understood by one of ordinary skill in the art to which this disclosure belongs. In addition, although preferable methods or samples are described in the present specification, descriptions similar or equivalent to these are included in the scope of the present disclosure. All publications mentioned herein as reference are incorporated by reference in their entirety.

According to one embodiment of the present disclosure, provided is a pharmaceutical composite formulation comprising a first layer comprising a proton pump inhibitor or a pharmaceutically acceptable salt thereof as an active ingredient, a disintegrant, and a binder; and a second layer comprising, as an active ingredient, an antacid selected from magnesium hydroxide, magnesium oxide, or a mixture thereof.

As used herein, the term "proton pump inhibitor (PPI)" refers to any drug that has pharmacological activity as an inhibitor of $H^+$-$K^+$ ATP-ase (proton pump), and forms of a PPI include salts, esters, amides, enantiomers, isomers, tautomers, prodrugs, and derivatives of known PPI inhibitory drugs. The final stage of gastric acid secretion in the body is the release of $H^+$-$K^+$ ATP-ase (proton pump) into the gastric lumen and the translocation of K ions into the gastric lumen, where the proton pump inhibitor strongly suppresses secretion of gastric acid by inhibiting the pump.

In one embodiment, the proton pump inhibitor may be one selected from the group consisting of esomeprazole, omeprazole, lansoprazole, rabeprazole, pantoprazole, and a mixture thereof.

Esomeprazole ((S)-5-methoxy-2-[(4-methoxy-3,5-dimethylpyridin yl)methylsulfinyl]-3H-benzimidazole) is the (S)-optical isomer known to have excellent safety and efficacy among the two optical isomers of omeprazole. Lansoprazole (2-{[3-methyl-4-(2,2,2-trifluoroethoxy)pyridin-2-yl]methanesulfinyl}-1H-1,3-benzodiazole) is marketed under the brand LANSTON™.

A pharmaceutically acceptable salt of the proton pump inhibitor is any pharmaceutically acceptable salt that may be commonly used in the art, and examples of the salt may include a metal salt such as a magnesium (Mg) salt, a strontium (Sr) salt, a lithium salt, a sodium salt, a potassium salt, or a calcium salt; or an ammonium salt, but embodiments are not limited thereto. Also, the proton pump inhibitor or a pharmaceutically acceptable salt thereof may be used in the form of an anhydride or a hydrate, such as a monohydrate, dihydrate, or trihydrate. For example, the proton pump inhibitor or a pharmaceutically acceptable salt thereof may be an esomeprazole magnesium salt or lansoprazole. For example, the proton pump inhibitor may be esomeprazole magnesium trihydrate.

As used herein, the term "disintegrant" refers to a material that absorbs moisture to promote disintegration of a formulation, and it may be used to improve dissolution of a drug. The disintegrant may be at least one selected from the group consisting of corn starch, crospovidone, polyvinylpyrrolidone (PVP), sodium starch glycolate, low-substituted hydroxypropyl cellulose, pregelatinized starch, alginic acid, sodium alginate, and a mixture thereof, but embodiments are not limited thereto.

In one embodiment, the disintegrant comprised in the first layer of the composite formulation may be one selected from the group consisting of crospovidone, sodium starch glycolate, and a mixture thereof.

The disintegrant has excellent compounding compatibility with the proton pump inhibitor. The disintegrant does not show discoloration when mixed with a proton pump inhibitor, such as esomeprazole, has excellent property stability, and may improve product quality by reducing the amount of related substances produced.

Residual solvents in pharmaceuticals refer to volatile organic chemicals used or generated in the manufacturing process of drug substances or excipients or the manufacturing process of formulations. Since all residual solvents have no therapeutic benefit, they must be removed to a level appropriate for product standards, Good Manufacturing Practice (GMP), or other quality standards (the Guideline for Residual Solvents in Drugs, Korea Food and Drug Administration). As a residual solvent analysis method, a chromatographic method such as gas chromatography is generally used. For example, croscarmellose sodium involves an extraction process of aqueous alcohols such as ethanol in the synthesis process (Handbook of Pharmaceutical Excipients 6th edition). Therefore, using croscarmellose sodium in the manufacturing process is not economical because an additional analysis of the residual ethanol solvent in the formulation is needed.

Since the disintegrant selected from the group consisting of crospovidone, sodium starch glycolate, and a mixture thereof, according to an embodiment, does not include ethanol and thus is not subjected to an ethanol residual solvent test. Thus, despite including the disintegrant, there is no hassle of separately performing an analysis of the ethanol residual solvent on the final formulation. Also, ethanol was found to have poor compounding stability with esomeprazole (FIG. 1B).

An amount of the disintegrant comprised in the first layer of the composite formulation according to an embodiment was sufficient to prevent acid decomposition of the proton pump inhibitor in the first layer of the composite formulation in the stomach and to dissolute at least about 80% of the proton pump inhibitor during 60 minutes of the dissolution test measurement.

An amount of the disintegrant comprised in the first layer of the composite formulation may be in a range of about 0.01 wt % to about 6.5 wt %, about 0.1 wt % to about 6 wt %, about 0.5 wt % to about 5.5 wt %, about 0.5 wt % to about 5 wt %, about 0.9 wt % to about 5 wt %, or about 1 wt % to about 5 wt %, based on the total weight of the first layer.

When the amount of the disintegrant is within these ranges, the proton pump inhibitor and the antacid present in different layers of the composite formulation show the release with the time difference for each layer, and as the antacid in the composite formulation is released first followed by releasing the proton pump inhibitor, gastric acid decomposition of the inhibitor may be prevented, and a desired dissolution rate may be obtained.

An amount of the disintegrant included in the first layer of the composite formulation according to an embodiment may be shown as based on the total weight of the formulation which may be in a range of about 0.01 wt % to about 5 wt %, for example, about 0.01 wt % to about 2.2 wt %, about 0.05 wt % to about 2 wt %, about 0.3 wt % to about 2 wt %, or about 0.1 wt % to about 1.7 wt %, based on the total weight of the formulation.

As used herein, the term "binder" refers to a material used to cause adhesion of powder particles in a formulation. The binder may be hydroxypropyl cellulose, hypromellose (hydroxypropyl methylcellulose), polyvinylpyrrolidone, pregelatinized starch, or a combination thereof, but embodiments are not limited thereto.

In one embodiment, the binder included in the first layer of the composite formulation may be one selected from the group consisting of hydroxypropyl cellulose, hypromellose, polyvinylpyrrolidone, and a mixture thereof.

An amount of the binder comprised in the first layer of the composite formulation according to an embodiment was sufficient to prevent acid decomposition of the proton pump inhibitor in the first layer of the composite formulation in the stomach and to dissolute at least about 80% of the proton pump inhibitor during 60 minutes of the dissolution test measurement. An amount of the binder included in the first layer of the composite formulation may be in a range of about 4 wt % to about 18 wt %, about 4 wt % to about 16 wt %, about 5 wt % to about 15 wt %, or about 7 wt % to about 14 wt %, based on the total weight of the first layer.

An amount of the binder included in the first layer of the composite formulation may be shown as based on the total weight of the formulation which may be in a range of about 0.01 wt % to about 5 wt %, for example, about 1 wt % to about 5 wt % or about 1.5 wt % to about 5.5 wt %, based on the total weight of the formulation.

In one embodiment, an amount of the binder included in the first layer of the composite formulation may be in a range of about 1.5 parts to about 4.5 parts by weight based on 1 part by weight of the disintegrant included in the first layer. For example, an amount of the binder may be in a range of about 1.5 parts to about 4.0 parts by weight or about 2 parts to about 4 parts by weight. For example, an amount of the binder included in the first layer of the composite formulation may be in a range of about 1.5 parts to about 4.5 parts by weight based on 1 part by weight of the disintegrant in the first layer, for example, crospovidone, sodium starch glycolate, and a mixture thereof.

In the first layer of the composite formulation according to an embodiment, an amount of the disintegrant may be in a range of about 0.5 wt % to about 5.5 wt % based on the total weight of the first layer, and an amount of the binder may be in a range of about 5 wt % to about 15 wt % based on the total weight of the first layer.

In the first layer of the composite formulation according to an embodiment, an amount of the disintegrant may be in a range of about 0.95 wt % to about 5 wt % based on the total weight of the first layer, and an amount of the binder may be in a range of about 5 wt % to about 15 wt % based on the total weight of the first layer.

Also, in the first layer of the composite formulation according to an embodiment, an amount of the disintegrant may be in a range of about 0.9 wt % to about 5 wt % based on the total weight of the first layer, and an amount of the binder may be in a range of about 5 wt % to about 15 wt % based on the total weight of the first layer.

Also, an amount of the disintegrant may be in a range of about 0.5 wt % to about 6 wt % based on the total weight of the first layer, and an amount of the binder may be in a range of about 1.5 parts to about 10 parts by weight based on 1 part by weight of the disintegrant in the first layer.

Also, an amount of the disintegrant may be in a range of about 0.9 wt % to about 5 wt % based on the total weight of the first layer, and an amount of the binder may be in a range of about 1.9 parts to about 4 parts by weight based on 1 part by weight of the disintegrant in the first layer.

When the amount of the disintegrant in the first layer of the composite formulation according to an embodiment is in a range of about 3 wt % to about 6 wt % based on the total weight of the first layer, the amount of the binder in the first layer may be in a range of greater than about 1 part to less than about 5 parts by weight based on 1 part by weight of the disintegrant. For example, an amount of the binder in the first layer of the composite formulation may be in a range of about 1.5 parts to about 4.5 parts by weight based on 1 part by weight of the disintegrant. For example, an amount of the binder in the first layer of the composite formulation may be in a range of about 1.5 parts to about 4.0 parts by weight or about 2 parts to about 4 parts by weight, based on 1 part by weight of the disintegrant.

Also, when an amount of the disintegrant may be in a range of about 3 wt % to about 5.5 wt % based on the total weight of the first layer, an amount of the binder may be in a range of about 1.5 parts to about 4.5 parts by weight based on 1 part by weight of the disintegrant in the first layer.

Also, when an amount of the disintegrant may be in a range of about 3 wt % to about 4 wt % based on the total weight of the first layer, an amount of the binder may be in a range of about 2 parts to about 4 parts by weight based on 1 part by weight of the disintegrant in the first layer.

When the amounts of the disintegrant and the binder are within these ranges, the proton pump inhibitor and the antacid present in different layers of the composite formulation may secure the release with the time difference for each layer, and as the formulation is controlled to release the antacid in the composite formulation first and then release the proton pump inhibitor, gastric acid decomposition of the drug may be prevented, and a desired dissolution rate of the proton pump inhibitor may be obtained.

As used herein, the term "antacid or antacid agent" refers to a compound capable of alleviating the typical feelings of heartburn (or pyrosis) of acid hypersecretion. Also, antacids refer to drugs that act either directly on excess gastric acid and gastroesophageal reflux, that is, by buffering the pH of the gastric mucosa, or indirectly by, for example, inhibiting acid secretion from the stomach. For example, antacids include substances that reduce all of the reported symptoms either indirectly by inhibiting acid secretion at the gastric level or directly by neutralizing effect of gastric acidity.

In one embodiment, the antacid may be magnesium hydroxide, magnesium oxide, sodium hydrogen carbonate, potassium carbonate, or a mixture thereof and may be preferably magnesium hydroxide, magnesium oxide, or a mixture thereof.

For example, an amount of the antacid may be in a range of about 2 parts to about 20 parts by weight, about 4 parts to about 16 parts by weight, or about 6 parts to about 10 parts by weight, based on 1 part by weight of the proton pump inhibitor or a pharmaceutically acceptable salt thereof included in the composite formulation. Also, an amount of the antacid may be in a range of about 1 wt % to about 70 wt %, about 10 wt % to about 60 wt %, about 20 wt % to about 55 wt %, or about 20 wt % to about 50 wt %, based on the total weight of the composite formulation. Also, an amount of the antacid may be in a range of about 1 wt % to about 90 wt %, about 10 wt % to about 80 wt %, or about 20 wt % to about 70 wt %, based on the total weight of the second layer.

The composite formulation may further include an additive selected from a diluent, a binder, a disintegrant, a lubricant, a fluidizer, and a mixture thereof. In one embodiment, the composite formulation may include a diluent, a binder, a disintegrant, a lubricant, or a mixture thereof in the first layer. In one embodiment, the composite formulation may include a diluent, a disintegrant, a fluidizer, a lubricant, or a mixture thereof in the first layer.

As used herein, the term "diluent" refers to a material that increases a volume of a formulation. The diluent may be at least one selected from the group consisting of microcrystalline cellulose, lactose, dextrin, mannitol, sorbitol, starch, calcium hydrogen phosphate, anhydrous calcium hydrogen phosphate, calcium carbonate, saccharides, and mixtures thereof, but embodiments are not limited thereto. For example, the total amount of the diluent included in the composite formulation is in a range of about 1 wt % to about 50 wt %, about 10 wt % to about 40 wt %, about 30 wt % to about 50 wt %, or about 20 wt % to about 30 wt %, based on the total weight of the formulation. Also, an amount of the diluent comprised in the first layer of the composite formulation is in a range of about 1 wt % to about 90 wt %, about 20 wt % to about 80 wt %, or about 40 wt % to about 75 wt %, based on the total weight of the first layer. An amount of the diluent comprised in the second layer of the composite formulation is in a range of about 1 wt % to about 60 wt %, about 10 wt % to about 50 wt %, or about 20 wt % to about 40 wt %, based on the total weight of the second layer.

As used herein, the term "binder" may be at least one selected from hydroxypropyl cellulose, hypromellose (hydroxypropyl methylcellulose), polyvinylpyrrolidone, pregelatinized starch, or a mixture thereof, but embodiments are not limited thereto. For example, the total amount of the binder in the formulation may be in a range of about 0.05 wt % to about 20 wt %, about 0.1 wt % to about 15 wt %, about 0.1 wt % to about 10 wt %, or about 1.0 wt % to about 5 wt %, based on the total weight of the formulation.

As used herein, the "disintegrant" refers to a material that is used to improve dissolution of a drug by promoting disintegration of a formulation, which may be at least one selected from the group consisting of croscarmellose sodium, corn starch, crospovidone, polyvinylpyrrolidone (PVP), sodium starch glycolate, low-substituted hydroxypropyl cellulose, pregelatinized starch, alginic acid, sodium alginate, and a mixture thereof, but embodiments are not limited thereto. For example, the total amount of the disintegrant in the formulation may be in a range of about 0.05 wt % to about 20 wt %, about 0.1 wt % to about 10 wt %, or about 1 wt % to about 5 wt %, based on the total weight of the formulation.

As used herein, the term "lubricant" refers to a material that improves the fluidity of the particulate materials to increase the filling property into a die, which is a lower part of the tableting machine, and thereby reduces the friction between the particulate materials or between the particulate materials, the punch, which is an upper part of the tableting machine, and the die to facilitate compression and release of tablets. The lubricant may be at least one selected from the group consisting of stearic acid, stearic acid salt, talc, corn starch, carnauba wax, light anhydrous silicic acid, magnesium silicate, synthetic aluminum silicate, hydrogenated oil, white wax, titanium oxide, microcrystalline cellulose, macrogol 4000 and 6000, isopropyl myristate, calcium hydrogen phosphate, talc, and mixtures thereof, but embodiments are not limited thereto. For example, the total amount of the lubricant included in the composite formulation may be in a range of about 0.01 wt % to about 10 wt %, about 0.05 wt % to about 5 wt %, about 0.5 wt % to about 3 wt %, or about 0.06 wt % to about 1 wt %, based on the total weight of the formulation. Also, an amount of the lubricant included in the first layer of the composite formulation may be in a range of about 0.05 wt % to about 20 wt %, about 0.1 wt % to about 10 wt %, or about 0.5 wt % to about 5 wt %, based on the total weight of the first layer in the formulation. An amount of the lubricant included in the second layer of the composite formulation may be in a range of about 0.01 wt % to about 10 wt %, about 0.01 wt % to about 5 wt %, or about 0.05 wt % to about 3 wt %, based on the total weight of the second layer in the formulation.

As used herein, the term "fluidizer" refers to a component that improves flow characteristics of active ingredients, excipients, or mixture thereof included in a composite formulation and may be included to maximize the effect while not affecting other components. The fluidizer may be at least one selected from the group consisting of silicon dioxide, colloidal silicon dioxide, talc, and mixtures thereof, but embodiments are not limited thereto. In one embodiment, the fluidizer included in the second layer of the composite formulation may be colloidal silicon dioxide. For example, the total amount of the fluidizer included in the composite formulation may be in a range of about 0 wt % to about 10 wt %, about 0.1 wt % to about 5 wt %, or about 0.5 wt % to about 3 wt %, based on the total weight of the formulation. An amount of the fluidizer included in the second layer of the composite formulation may be in a range of about 0 wt % to about 10 wt %, about 0.5 wt % to about 5 wt %, or about 1 wt % to about 3 wt %, based on the total weight of the second layer in the formulation.

An amount of the disintegrant included in the second layer of the composite formulation according to an embodiment may be in a range of about 0 wt % to about 10 wt %, about 0.1 wt % to about 7 wt %, about 0.1 wt % to about 5 wt %, or about 1 wt % to about 3 wt %, based on the total weight of the second layer in the formulation.

An amount of the disintegrant included in the second layer of the composite formulation may be shown as based on the total weight of the formulation which may be in a range of about 0.01 wt % to about 5 wt %, for example, about 0.05 wt % to about 3 wt % or about 0.5 wt % to about 2.5 wt %, based on the total weight of the formulation.

Additionally, any pharmaceutical additive that may be commonly used in the art may be included in the formulation in an appropriate amount. For example, at least one additive selected from the group consisting of a surfactant, an antioxidant, a preservative, a stabilizer, a flavoring agent, a colorant, a solubilizers, a pH adjusting agent, a coating agent, and any combination thereof may be further included, and embodiments are not limited thereto.

The coating agent may be at least one selected from the group consisting of polyvinyl alcohol (PVA), hydroxypropylmethyl cellulose (HPMC), hydroxypropyl cellulose (HPC), and mixtures thereof, but embodiments are not limited thereto.

The composite formulation according to an embodiment may be a tablet, a capsule, or a granule. For example, the composite formulation may be in the form of a multi-layer tablet, such as a double-layer tablet or a three-layer tablet, or, a tablet-in-tablet, wherein the hardness of the tablet may be, for example, in a range of about 10 kP to about 20 kP. For example, when the composite formulation is a double-layer tablet, the composite formulation may comprise: a first layer comprising a proton pump inhibitor or a pharmaceutically acceptable salt thereof as an active ingredient, a disintegrant, and a binder; and a second layer comprising, as an active ingredient, an antacid selected from magnesium hydroxide, magnesium oxide, or a mixture thereof.

Also, for example, when the composite formulation is a three-layer tablet, the composite formulation may comprise: a first layer comprising a proton pump inhibitor or a pharmaceutically acceptable salt thereof as an active ingredient, a disintegrant, and a binder; a second layer comprising, as an active ingredient, an antacid selected from magnesium hydroxide, magnesium oxide, or a mixture thereof; and at least one other layer.

Also, for example, when the composite formulation is a double-layer tablet, the composite formulation may comprise: an inner layer comprising a proton pump inhibitor or a pharmaceutically acceptable salt thereof as an active ingredient, a disintegrant, and a binder; and an outer layer comprising, as an active ingredient, an antacid selected from magnesium hydroxide, magnesium oxide, or a mixture thereof.

The composite formulation according to an embodiment may be a multi-layer tablet, for example, a double-layer tablet, and the proton pump inhibitor and the antacid present in different layers may be released with the time difference for each layer. For example, when the antacid present in the layer containing the antacid of the composite formulation is first released to increase the pH in the stomach, and then the proton pump inhibitor present in the layer containing the proton pump inhibitor is released to neutralize the acidic environment in the stomach, decomposition of the proton pump inhibitor by gastric acid may be prevented.

The composite formulation is a pharmaceutical composite formulation comprising a proton pump inhibitor and an antacid as active ingredients, and unlike commercially available enteric formulations, the antacid in the composite formulation quickly neutralizes gastric acid without enteric coating to prevent the decomposition of the proton pump inhibitor, and the proton pump inhibitor is rapidly eluted and absorbed in the body, which does not delay the expression of the drug efficacy.

In addition, the composite formulation prevents decomposition of the proton pump inhibitor in the stomach according to the release with the time difference of the proton pump inhibitor and the antacid, improves stability, and thus may provide a pharmaceutical composite formulation showing an optimal drug release pattern. In one embodiment, the total amount of related substances of the proton pump inhibitor or a pharmaceutically acceptable salt thereof in the composite formulation is based on 2.0 wt % or less with respect to the total weight of the proton pump inhibitor or a pharmaceutically acceptable salt thereof. The total amount of related substances may be stored in a chamber of severe stability conditions of 60° C. for 7 days and measured under the test conditions of Experimental Example 2.

In one embodiment, when a test is conducted in a mixture solution including 75 mL of 0.1 N HCl and 225 mL of purified water at about 75 revolutions per minute (rpm) at a temperature of 37±0.5° C. according to the second method (paddle method) of the dissolution test of the United States Pharmacopeia (USP), the composite formulation simultaneously has, for 10 minutes, a dissolution rate of the proton pump inhibitor in a range of about 10% to about 50% and a dissolution rate of the antacid of about 70% or higher. The dissolution test may be measurement using two tablets of the composite formulation according to an embodiment.

In one embodiment, the composite formulation may simultaneously have a dissolution rate of the proton pump inhibitor in a range of about 5% to about 30% and a dissolution rate of the antacid of about 60% or more.

As used herein, the numeral ranges represented using the term "to" include ranges that have numerical values shown before and after "to" as the lower limit and the upper limit, respectively. The term "about" or "approximately" denotes that the referenced value may vary to some extent. For example, the value may vary 10%, 5%, 2%, or 1%. For example, the expression "about 5" includes any value between 4.5 and 5.5, between 4.75 and 5.25, between 4.9 and 5.1, or between 4.95 and 5.05. As used herein, numerical values are regarded as including the meaning of "about" even when not specified.

The term "has", "may have", "include", or "may include" indicates the presence of the corresponding characteristics (e.g., numerical values or elements such as components), and does not exclude the presence of additional characteristics.

Hereinafter, the present disclosure will now be described in detail with reference to the following examples. However, these examples are only for illustrative purposes and are not intended to limit the scope of the one or more embodiments of the present disclosure.

EXAMPLES

Examples 1 to 6: Preparation of Double-Layer Tablets Including Esomeprazole and Magnesium Hydroxide Double-layer tablets including esomeprazole as an active ingredient and a magnesium hydroxide as an antacid according to compositions shown in Table 1.

Esomeprazole magnesium trihydrate (40 mg as esomeprazole), microcrystalline cellulose (AVICEL™ PH101), hydroxypropyl cellulose, crospovidone, and sodium starch glycolate were mixed for 10 minutes. A sodium stearyl fumarate as a lubricant was added to the mixture and mixed for 5 minutes to prepare a final mixture of the upper layer parts.

Magnesium hydroxide, microcrystalline cellulose (PH101), and crospovidone were mixed for 10 minutes. The mixture was compressed using a roller compressor (TF-1-A60, Freund vector) at a hydraulic pressure of 5 MPa, a feeder speed of 5 rpm, and a roller speed of 1 rpm to form flakes, and the flakes were classified with a sieve having a mesh size of 0.8 mm. A colloidal silicon dioxide (Aerosil) as a fluidizer was added to the classified resultant and mixed for 5 minutes, and then a sodium stearyl fumarate as a lubricant was added to the mixture and mixed for 5 minutes to prepare a final mixture of the lower parts. In Example 4, sodium starch glycolate was added instead of crospovidone.

The final mixture of the upper part and the final mixture of the lower part were compressed into a table using a tableting machine (AUTOTAB-200TR, Ichihashi Seiki) to prepare a double-layer tablet (having a hardness of 18 kp).

The compositions of the pharmaceutical composite formulations according to Examples 1 to 6 are shown in Table 1.

TABLE 1

| Component (unit: mg) | Example 1 | Example 2 | Example 3 | Example 4 | Example 5 | Example 6 |
|---|---|---|---|---|---|---|
| Esomeprazole magnesium trihydrate | 44.5 | 44.5 | 44.5 | 44.5 | 44.5 | 44.5 |
| Microcrystalline cellulose | 184.9 | 178.5 | 174.5 | 178.5 | 185.5 | 167.5 |
| Hydroxypropyl cellulose | 25.0 | 25.0 | 25.0 | 25.0 | 18.0 | 36.0 |
| Crospovidone | 2.6 | 9.0 | 13.0 | — | 9.0 | 9.0 |
| Sodium starch glycolate | — | — | — | 9.0 | — | — |
| Sodium stearyl fumarate | 3.0 | 3.0 | 3.0 | 3.0 | 3.0 | 3.0 |
| Total amount of upper layer | 260.0 | 260.0 | 260.0 | 260.0 | 260.0 | 260.0 |
| Magnesium hydroxide | 350.0 | 350.0 | 350.0 | 350.0 | 350.0 | 350.0 |
| Microcrystalline cellulose | 135.0 | 135.0 | 135.0 | 135.0 | 135.0 | 135.0 |
| Crospovidone | 15.0 | 15.0 | 15.0 | — | 15.0 | 15.0 |
| Colloidal silicon dioxide | 15.0 | 15.0 | 15.0 | 15.0 | 15.0 | 15.0 |
| Sodium starch glycolate | — | — | — | 15.0 | — | — |
| Sodium stearyl fumarate | 5.0 | 5.0 | 5.0 | 5.0 | 5.0 | 5.0 |
| Total amount of lower layer | 520.0 | 520.0 | 520.0 | 520.0 | 520.0 | 520.0 |
| Total amount of uncoated tablet | 780.0 | 780.0 | 780.0 | 780.0 | 780.0 | 780.0 |

COMPARATIVE EXAMPLES

Comparative Examples 1 to 6: Preparation of Double-Layer Tablets Including Esomeprazole and Magnesium Hydroxide Double-layer tablets were prepared in the same manner in Example 1 according to compositions shown in Table 2. The compositions of the pharmaceutical composite formulations according to Comparative Examples 1 to 6 are shown in Table 2.

TABLE 2

| Component (unit: mg) | Comparative Example 1 | Comparative Example 2 | Comparative Example 3 | Comparative Example 4 | Comparative Example 5 | Comparative Example 6 |
|---|---|---|---|---|---|---|
| Esomeprazole magnesium trihydrate | 44.5 | 44.5 | 44.5 | 44.5 | 44.5 | 44.5 |

TABLE 2-continued

| Component (unit: mg) | Comparative Example 1 | Comparative Example 2 | Comparative Example 3 | Comparative Example 4 | Comparative Example 5 | Comparative Example 6 |
|---|---|---|---|---|---|---|
| Microcrystalline cellulose | 187.5 | 169.5 | 178.5 | 203.5 | 194.5 | 158.5 |
| Hydroxypropyl cellulose | 25.0 | 25.0 | 25.0 | — | 9.0 | 45.0 |
| Crospovidone | — | 18.0 | — | 9.0 | 9.0 | 9.0 |
| Croscarmellose sodium | — | — | 9.0 | — | — | — |
| Sodium stearyl fumarate | 3.0 | 3.0 | 3.0 | 3.0 | 3.0 | 3.0 |
| Total amount of upper layer | 260.0 | 260.0 | 260.0 | 260.0 | 260.0 | 260.0 |
| Magnesium hydroxide | 350.0 | 350.0 | 350.0 | 350.0 | 350.0 | 350.0 |
| Microcrystalline cellulose (PH101) | 135.0 | 135.0 | 135.0 | 135.0 | 135.0 | 135.0 |
| Crospovidone | 15.0 | 15.0 | — | 15.0 | 15.0 | 15.0 |
| Croscarmellose sodium | — | — | 15.0 | — | — | — |
| Colloidal silicon dioxide | 15.0 | 15.0 | 15.0 | 15.0 | 15.0 | 15.0 |
| Sodium stearyl fumarate | 5.0 | 5.0 | 5.0 | 5.0 | 5.0 | 5.0 |
| Total amount of lower layer | 520.0 | 520.0 | 520.0 | 520.0 | 520.0 | 520.0 |
| Total amount of uncoated tablet | 780.0 | 780.0 | 780.0 | 780.0 | 780.0 | 780.0 |

EXPERIMENTAL EXAMPLES

Experimental Example 1: Property Stability Test

The changes in properties of the pharmaceutical composite formulations were measured under the following conditions to confirm compatibilities of the other components (e.g., excipients or antacids) and esomeprazole included in the composite formulations, and the change tendencies are shown in FIG. 1.

<Compatibility>

After mixing esomeprazole and each of the other components at a weight ratio of 1:1, the mixtures of a predetermined amount were each compressed into a tablet of 200 kgf using a tableting machine (AUTOTAB-200TR, Ichihashi Seiki). Each of the prepared tablets was packaged in an HDPE bottle and stored in a chamber under severe stability conditions at 60° C. for 7 days. The changes in properties of the tablets prepared by varying other components mixed with esomeprazole are shown in FIG. 1A when 7 days for storage.

In FIG. 1A, a formulation only including esomeprazole as an active ingredient and not including other components was used as a Control group. Also, as the other components which are included together with esomeprazole, each of the Test groups included one excipient selected from microcrystalline cellulose (MCC), low-substituted hydroxypropyl cellulose (HPC-L), croscarmellose sodium (PRIMELLOSE™), croscarmellose sodium (ACDISOL™), crospovidone (POLYPLASDONE™ XL-10), and crospovidone (KOLLIDON CL™), or magnesium hydroxide (Mg(OH)₂) as an antacid, and the tablets were indicated by the names of the excipients or antacids. FIG. 1A shows the tablets of the Control group and Test groups after 7 days of storage in the chamber.

FIG. 1A shows the property change tendency of the tablets according to the compatibilities of esomeprazole and the other components. As shown in FIG. 1A, when croscarmellose sodium (PRIMELLOSE™ or ACDISOL™) was used as an excipient, discoloration of the tablets was observed with the naked eye, indicating poor stability in the property. Also, since croscarmellose sodium contains ethanol, a residual solvent test needs to be separately performed when croscarmellose sodium is included as an excipient.

When the formulations included the other component, such as microcrystalline cellulose (MCC), low-substituted hydroxypropyl cellulose (HPC-L), crospovidone (POLYPLASDONE™ XL-10), or crospovidone (KOLLIDON CL™) as an excipient component or magnesium hydroxide (Mg(OH)₂) as an antacid, the change was insignificant. Also, since the excipient component does not contain ethanol as a residual solvent, a residual solvent test does not need to be performed.

In addition, after mixing esomeprazole and ethanol at a weight ratio of 5:1, the mixture was stored in a chamber under severe stability conditions at 60° C. for 7 days. FIG. 1B shows property change tendency according to compatibility of esomeprazole and ethanol.

Changes in properties were observed before (left of FIG. 1B) and after (right of FIG. 1B) storing a mixture of esomeprazole and ethanol for 7 days. As shown in FIG. 1B, it may be known that discoloration occurred as the color was significantly changed by the mixing of esomeprazole and ethanol, as compared to the initial color.

Figure 1C:
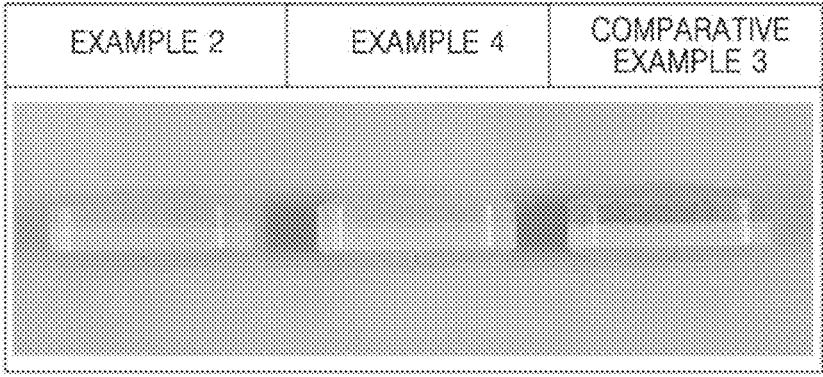
FIG. 1C shows changes in properties of composite formulations prepared in Examples 2 and 4 and Comparative Example 3.

Also, the composite formulations prepared in Examples 2 and 4 and Comparative Example 3 were each packaged in an HDPE bottle, stored in a chamber under severe stability conditions at 60° C. for 7 days, and the changes in properties were observed. FIG. 1C shows property change tendency of composite formulations prepared in Examples 2 and 4 and Comparative Example 3. As shown in FIG. 1C, as compared to Example 2 or 4 after 7 days of storage in the chamber, the formulation of Comparative Example 3 including croscarmellose sodium as a disintegrant had significant color change as compared to the initial color, and thus it may be known that discoloration occurred in the formulation of Comparative Example 3.

Experimental Example 2: Related Substance Test of Esomeprazole

Figure 2:
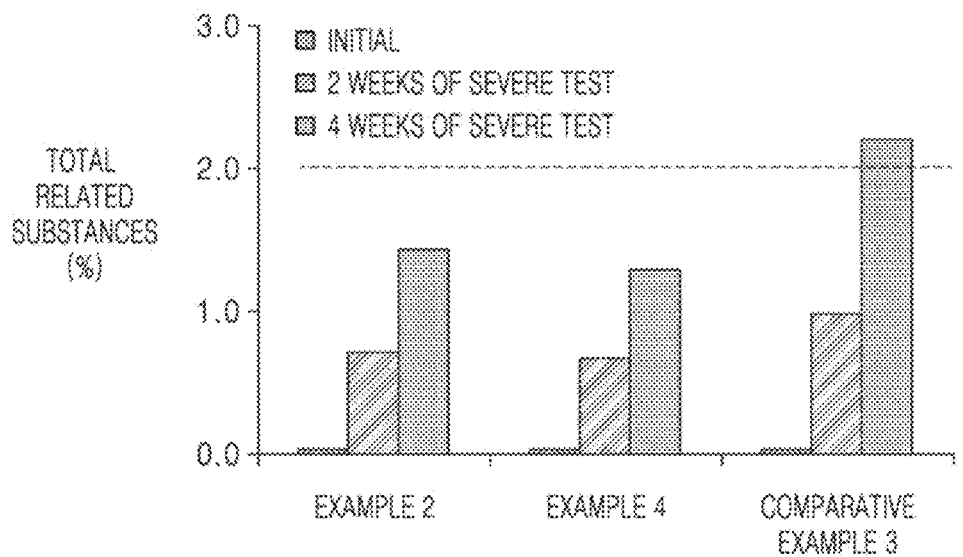
FIG. 2 is a graph showing total related substance contents (%) of the composite formulations prepared in Examples 2 and 4 and Comparative Example 3 according to a test in severe conditions.

In order to confirm stability by the formulations prepared in Examples 2 and 4 and Comparative Example 3, a severe test was performed under the same conditions with those of Experimental Example 1, the total amounts of the related substances produced from the formulations according to the analysis conditions were measured.
<Analysis Conditions>
Column: HYPERSIL BDS C18 100 mm×4.6 mm, 3 μm (column temperature: 25° C.)
Mobile phase A: acetonitirle:phosphate buffer (pH 7.6): water=100:100:800
Mobile phase B: acetonitirle:phosphate buffer (pH 7.6): water=800:10:190
(Phosphate buffers (pH 7.6) of the mobile phases A and B were each mixed with 5.2 mL of 1.0 mol/L sodium dihydrogen phosphate and 63.0 mL of 0.5 mol/L disodium hydrogen phosphate, and water was added thereto to prepare 1 L of the buffer.)
Detector: Ultraviolet absorbance spectrometer (measurement wavelength 302 nm)
Flow rate: 1.0 mL/min
Injection volume: 20 μL
Sample temperature: 4° C.
FIG. 2 is a graph showing total related substance contents (%) of the composite formulations prepared in Examples 2 and 4 and Comparative Example 3 according to a severe test.
When the formulations prepared in Examples 2 and 4 and Comparative Example 3 were each packaged in an HDPE bottle and stored for 7 days in the chamber under severe conditions at 60° C. to perform the severe test for 4 weeks, as shown in FIG. 2, it may be known that the total amounts of the related substances produced from the formulations prepared in Examples 2 and 4 had were reduced compared to Comparative Example 3, satisfied the standard of 2.0% or lower of the related substance, and had excellent stability. On contrary, the formulation prepared in Comparative Example 3 after 4 weeks of the severe test had the total amount of the related substance greater than 2.0%.
From the results of the property stability and related substance evaluation according to Experimental Examples 1 and 2, it may be confirmed that crospovidone or sodium starch glycolate had better compatibility with esomeprazole than that of croscarmellose sodium which contains ethanol as the residual solvent, and that the formulation including crospovidone or sodium starch glycolate as a disintegrant instead of croscarmellose sodium had relatively excellent stability.

Experimental Example 3: Dissolution Test of Esomeprazole

Figure 3:
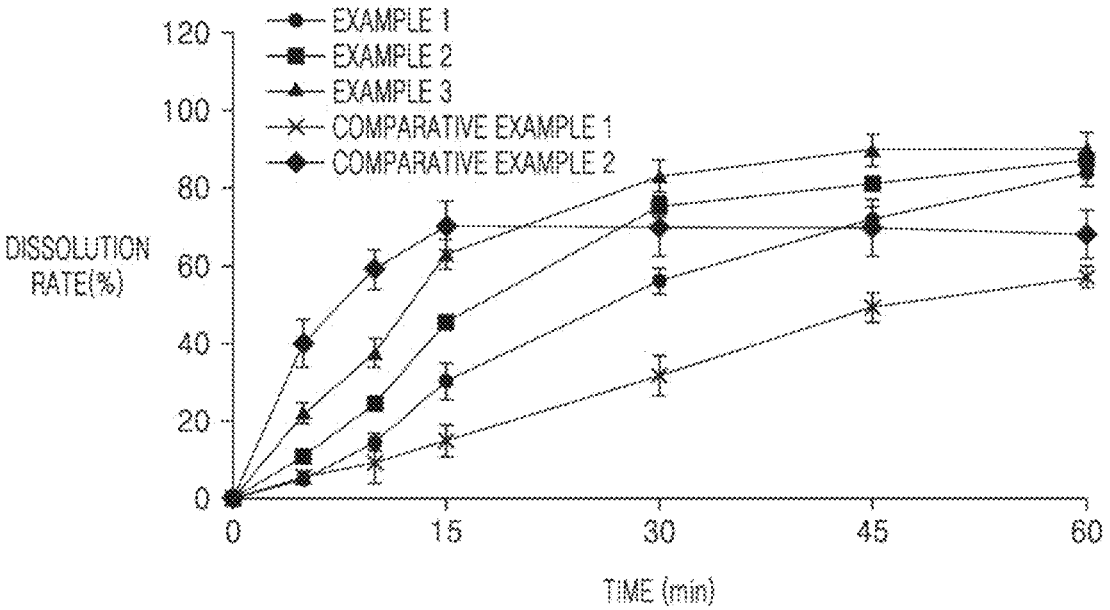
FIG. 3 is a graph showing dissolution rate (%) of esomeprazole according to dissolution time (min.) of the composite formulations prepared in Examples 1 to 3 and Comparative Examples 1 and 2.
Figure 4:
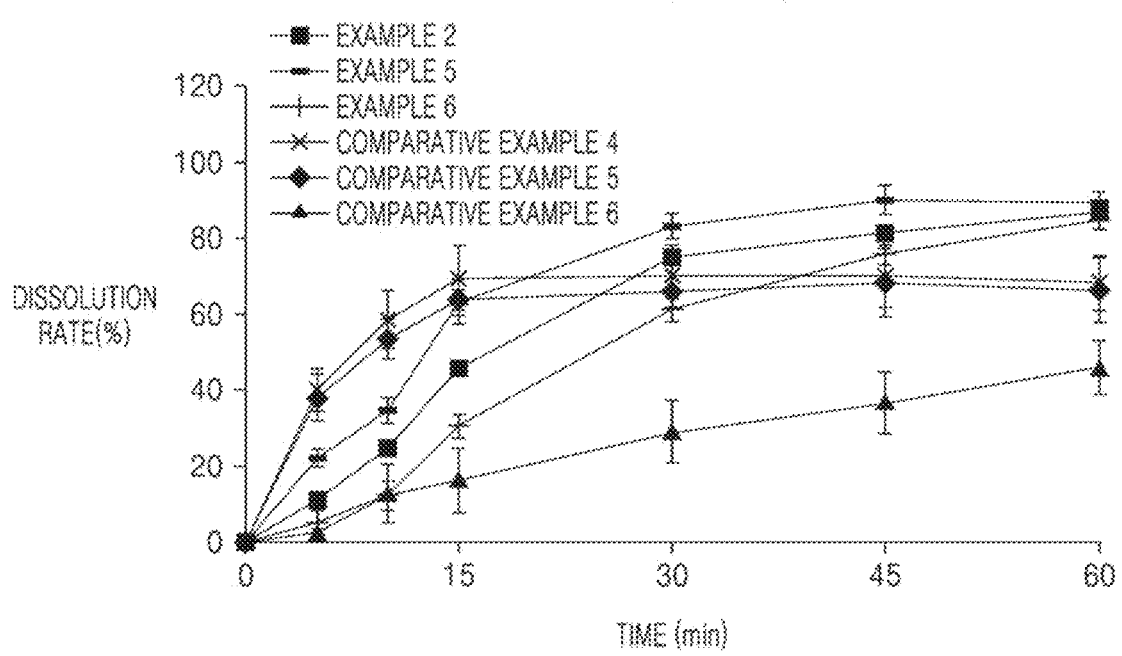
FIG. 4 is a graph showing dissolution rate (%) of esomeprazole according to dissolution time (min.) of the composite formulations prepared in Examples 2, 5, and 6 and Comparative Examples 4 to 6.

Under the following dissolution conditions and analysis conditions, dissolution rates of esomeprazole from the formulations prepared in Examples 1 to 3 and 5 and 6 and Comparative Examples 1 and 2 and 4 to 6 were evaluated, and the results are shown in FIGS. 3 and 4.

<Dissolution Conditions>
Eluate: 2 tablets (40 mg of esomeprazole per tablet, the total of 80 mg) are tested in a solution prepared by mixing 75 mL of 0.1 N HCl and 225 mL of purified water.
Apparatus: 2nd method (paddle method) of the dissolution test of the United States Pharmacopoeia (USP), 75±2 rpm
Temperature: 37±0.5° C.
Dissolution time: 5, 10, 15, 30, 45, 60 minutes
(The collected eluate is filtered through a 0.45 μm membrane filter, and then immediately mixed with 0.25 M NaOH at a ratio of 5:1 to be tested).
<Analysis Conditions>
Column: INERTSIL ODS-3V 150 mm×4.6 mm, 5 μm (column temperature: 25° C.)
Mobile phase: acetonitirle:phosphate buffer (pH 7.3): water=350:500:150
(A phosphate buffer (pH 7.3) of the mobile phase was mixed with 10.5 mL of 1 mol/L sodium dihydrogen phosphate and 60.0 mL of 0.5 mol/L disodium hydrogen phosphate, and water was added thereto to prepare 1 L of the buffer.)
Detector: Ultraviolet absorbance spectrometer (measurement wavelength 302 nm)
Flow rate: 1.0 mL/min
Injection volume: 20 μL
Sample temperature: 25° C.
Under these conditions, the eluate prepared by mixing 0.1 N HCl and purified water represents the gastric juice present as 0.1 N HCl in the stomach and purified water as the water taken together with the drug by humans to verify the degree of decomposition of esomeprazole, which is a proton pump inhibitor (PPI) that may be decomposed in a low pH when taken by humans, and the antacid strength of the antacid.
FIG. 3 is a graph showing dissolution rate (%) of esomeprazole according to dissolution time (min.) of the composite formulations prepared in Examples 1 to 3 and Comparative Examples 1 and 2. Difference between dissolution rates of esomeprazole according to amounts of the disintegrant in the composite formulations may be confirmed by FIG. 3.
The formulations of Examples 1 to 3 included about 1 wt %, about 3.5 wt %, and about 5 wt % of crospovidone as a disintegrant in the first layer, each respectively, based on the total weight of the first layer; and the formulations of Comparative Examples 1 and 2 included about 0 wt % and about 7 wt % of crospovidone as a disintegrant in the first layer, each respectively, based on the total weight of the first layer. As shown in FIG. 3, there was difference between the dissolution rates of esomeprazole according to the amounts of the disintegrant in the first layer of the double-layer tablets.
Referring to FIG. 3, the dissolution rate of esomeprazole was the lowest in Comparative Example 1, and the dissolution appeared slowly due to the lack of disintegrating strength of the double-layer tablet. In the case of Comparative Example 2, referring to the results of FIG. 6, the dissolution of esomeprazole appeared faster than the pH increase of the dissolution test solution by the antacid of the second layer, and thus the acid decomposition of esomeprazole increased. The formulations of Examples 1 to 3 had dissolution rates of about 80% or higher for 20 minutes of the dissolution test measurement, and thus it was deemed that most of esomeprazole in the tablets were eluted without acid decomposition within 60 minutes, and the dissolution speeds were different according to the amount of the disintegrant. In the formulations of Examples 1 to 3, the active ingredients in the composite formulation show the release with the time difference for each layer according to the types and amounts of the excipients in the composite formulation and the antacid in the second layer of the formulation, and thus it is deemed that the formulations have a significant prevention effect on the acid decomposition of esomeprazole. Accordingly, it is expected that the PPI formulation, which is unstable in a low pH, may be developed into a short-acting formulation without delay in drug expression to provide improved convenience in its administration.

FIG. 4 is a graph showing dissolution rate (%) of esomeprazole according to dissolution time (min.) of the composite formulations prepared in Examples 2, 5, and 6 and Comparative Examples 4 to 6.

The formulation of Example 2 was selected to include the same amount of disintegrant (an amount of the disintegrant included was 3.5 wt % based on the total weight of the first layer), but in Examples 5 and 6, the content ratios of the binder were changed to prepared the formulations. Accordingly, Examples 2, 5, and 6 each included a binder with respect to the disintegrant in a weight ratio of about 3:1, about 2:1, and about 4:1, respectively, in the first layer of each of the composite formulations. Also, the composite formulation of Comparative Example 4 did not include a binder, and the composite formulations of Comparative Examples 5 and 6 included a binder with respect to the disintegrant in a weight ratio of about 1:1 and about 5:1, respectively, in the first layer. FIG. 4 shows the dissolution result of esomeprazole according to the ratios of the binder and the disintegrant included in the first layer of the composite formulations.

As shown in FIG. 4, the composite formulations of Examples 2, 5, and 6 had difference in the dissolution rates depending on the amount of binder, but the final dissolution rates at 60 minutes showed a similar pattern. It is deemed that the formulations have a significant prevention effect on the acid decomposition of esomeprazole due to the release with the time difference for each layer and the antacid in the second layer. On contrary, the composite formulation of Comparative Example 4 showed a low dissolution rate, and it was deemed that as the formulation only included the disintegrant without a binder, the effect of the release with the time difference with that of the second layer was reduced, and thus acid decomposition of esomeprazole occurred. Also, the composite formulation of Comparative Example 5 included the binder with respect to the disintegrant in a weight ratio of about 1:1, and showed a low dissolution rate similar to that of the composite formulation of Comparative Example 4. The composite formulation of Comparative Example 6 contained a relatively large amount of the binder and thus showed a low dissolution rate and a slow dissolution speed during 60 minutes of the measurement. The formulation of Comparative Example 6 showed a large deviation when measuring the dissolution rate, and it seems that the excessive amount of the binder contained in the first layer under the dissolution test conditions weakened the antacid strength of the antacid of the second layer. Accordingly, it is considered that there will be problems that a uniform drug administration effect may not be expected when the drug is administrated, and that onset of drug action may appear relatively slow. From the result of FIG. 4, in order to increase the release effect with the time difference between the antacid and the PPI drug, and at the same time to obtain a fast-acting PPI formulation, it is effective that the binder with respect to the disintegrant is included with a weight ratio of about 2:1 to about 4:1 in the first layer of the combination formulation.

Experimental Example 4: Dissolution Test of Magnesium Hydroxide

Figure 5:
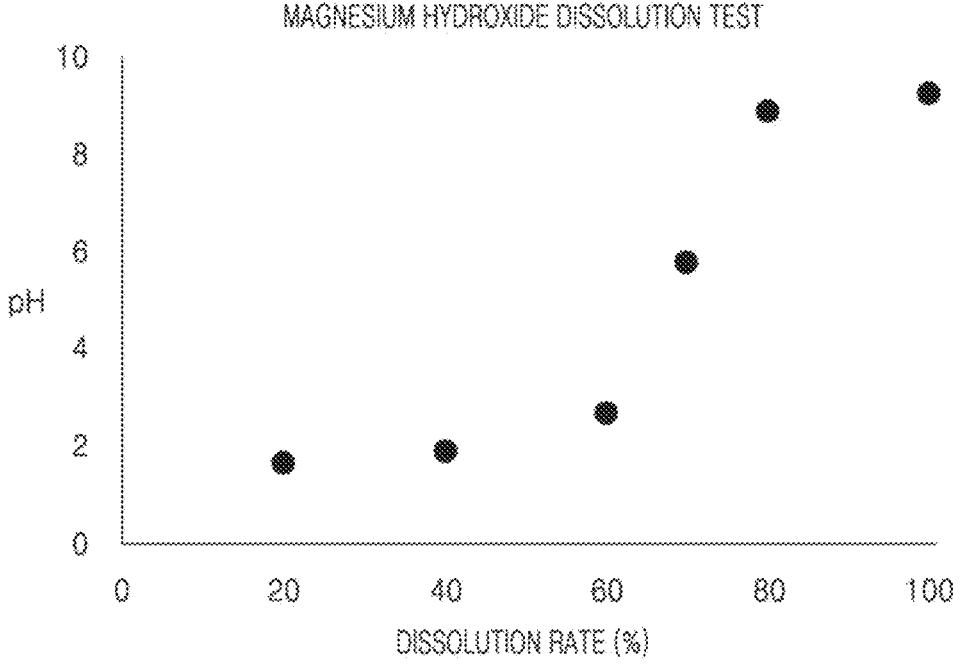
FIG. 5 is a graph showing pH of the composite formulation according to dissolution rate (%) of magnesium hydroxide included in the composite formulation prepared in Example 2.
Figure 6:
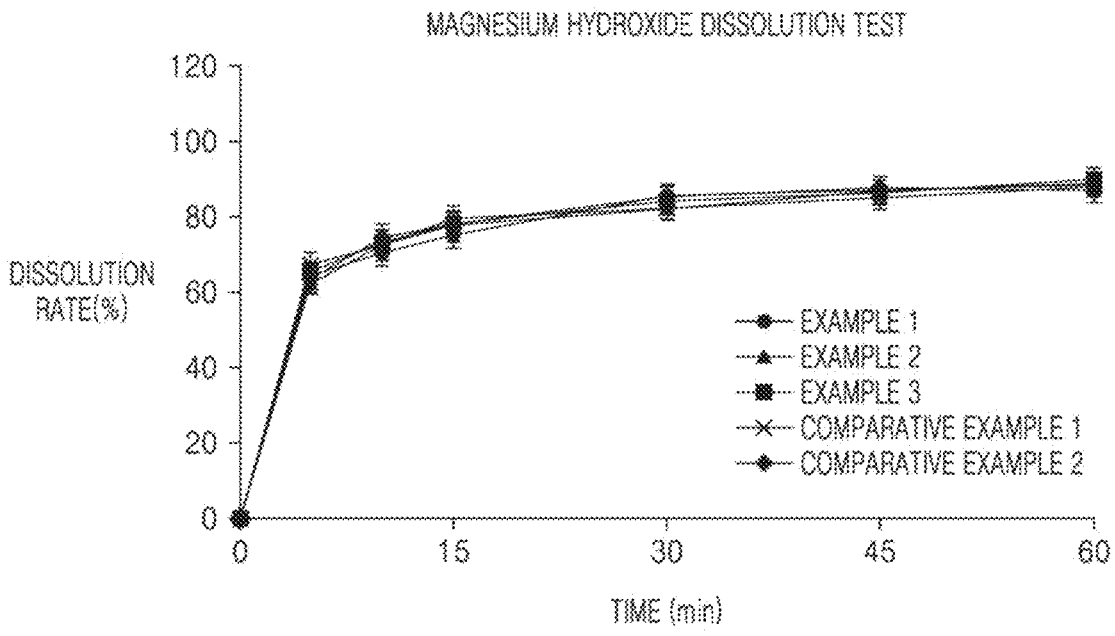
FIG. 6 is a graph showing dissolution rate (%) of magnesium hydroxide according to dissolution time (min.) of the composite formulations prepared in Examples 1 to 3 and Comparative Examples 1 and 2.

The dissolution rates of magnesium hydroxide of the composite formulations prepared in Examples 1 to 3 or Comparative Examples 1 and 2 under the following dissolution conditions and analysis conditions were measured, and the results are shown in FIGS. 5 and 6.

<Dissolution Conditions>

Eluate: 2 tablets (40 mg of esomeprazole per tablet, the total of 80 mg) are tested in a solution prepared by mixing 75 mL of 0.1 N HCl and 225 mL of purified water.

Apparatus: The 2nd method (paddle method) of the United States Pharmacopoeia (USP), 75±2 rpm Temperature: 37±0.5° C.

<Analysis Conditions>

Detector: Atomic absorbance spectrometer

Lamp: Magnesium hollow cathode lamp

Wavelength: 285.2 nm

Gas used: Air-Acetylene

FIG. 5 is a graph showing pH of the composite formulation according to dissolution rate (%) of magnesium hydroxide included in the composite formulation prepared in Example 2. As shown in FIG. 5, pH of the composite formulation was measured using the eluate of Experimental Example 4 when magnesium hydroxide in the second layer was dissoluted 20%, 40%, 60%, 70%, 80%, and 100%.

In FIG. 5, since about 60% to about 80% of magnesium hydroxide was dissolved at an inflection point where the pH rapidly changed, it may be known that acid decomposition of the proton pump inhibitor, e.g., esomeprazole, in the composite formulation prepared in Example 2 may be effectively prevented based on this point. In particular, FIG. 5 shows that the pH started to rapidly increase when about 60% of magnesium hydroxide was dissoluted, and thus it may be known that the proton pump inhibitor in the composite formulation may be preferably dissolved when magnesium hydroxide is about 60% or more released to secure stability.

FIG. 6 is a graph showing dissolution rate (%) of magnesium hydroxide according to dissolution time (min.) of the composite formulations prepared in Examples 1 to 3 and Comparative Examples 1 and 2.

As shown in FIG. 6, magnesium hydroxide in the second layer of the composite formulation prepared in Example 2 showed dissolution rates of about 64% and about 70% at 5 minutes and 10 minutes, respectively. Magnesium hydroxide in the second layer of the composite formulations prepared in Example 1 to 3 and Comparative Examples 1 and 2 showed all the similar dissolution rate pattern, and it may be known that dissolution of magnesium hydroxide is not influenced by the composition of the first layer in the composite formulation.

In consideration of both the results of FIG. 6 and the results of FIG. 3, acid decomposition of esomeprazole in the composite formulation prepared in Example 2 was effectively prevented, and thus it was confirmed that that the composite formulation exhibited a stable dissolution rate of esomeprazole.

In consideration of both the results of FIG. 6 and the results of FIGS. 3 and 4, esomeprazole in the first layer of the composite formulations prepared in Comparative Examples 2, 5, and 6 was eluted about 30% or more and about 50% or more at 5 minutes and 10 minutes, respectively, which was a faster dissolution rate than that of magnesium hydroxide, and it was confirmed that the composite formulations had unstable dissolution rates due to acid decomposition of esomeprazole in an acid environment.

While the exemplary embodiments have been particularly shown and described with reference to the exemplary embodiments thereof, it will be understood by those of ordinary skill in the art that various changes in form and details may be made therein without departing from the spirit and scope of the exemplary embodiments as defined by the following claims. The described embodiments should be considered in descriptive sense only and not for purposes of limitation. Therefore, the scope of the disclosure is defined not by the detailed description of the disclosure but by the appended claims (and equivalents thereof), and all differences within the scope will be construed as being included in the present disclosure.

The invention claimed is:

1. A pharmaceutical composite formulation comprising:
a first layer comprising a proton pump inhibitor or a pharmaceutically acceptable salt thereof as an active ingredient, a first disintegrant, and a binder; and
a second layer comprising, as an active ingredient, an antacid selected from the group consisting of magnesium hydroxide, magnesium oxide, er and a mixture thereof, and a second disintegrant,
wherein the proton pump inhibitor is esomeprazole or a pharmaceutically acceptable salt thereof,
wherein the first disintegrant in the first layer is selected from the group consisting of crospovidone, sodium starch glycolate, and a mixture thereof,
wherein an amount of the first disintegrant in the first layer is in a range of about 0.5 wt % to about 5.5 wt % based on a total weight of the first layer,
wherein the second disintegrant in the second layer is selected from the group consisting of crospovidone, sodium starch glycolate, and a mixture thereof,
wherein the binder is hydroxypropyl cellulose, and
wherein an amount of the binder is in a range of about 1.5 parts to about 4.5 parts by weight based on 1 part by weight of the first disintegrant in the first layer.

2. The pharmaceutical composite formulation of claim 1, wherein the amount of the binder is in a range of about 5 wt % to about 15 wt % based on the total weight of the first layer.

3. The pharmaceutical composite formulation of claim 1, wherein the amount of the first disintegrant is in a range of about 0.9 wt % to about 5 wt % based on the total weight of the first layer, and the amount of the binder is in a range of about 1.9 parts to about 4.5 parts by weight based on 1 part by weight of the first disintegrant in the first layer.

4. The pharmaceutical composite formulation of claim 1, wherein the amount of the first disintegrant is in a range of about 0.95 wt % to about 5 wt % based on the total weight of the first layer, and the amount of the binder is in a range of about 5 wt % to about 15 wt % based on the total weight of the first layer.

5. The pharmaceutical composite formulation of claim 1, wherein the composite formulation is a double-layer tablet.

6. The pharmaceutical composite formulation of claim 1, wherein the composite formulation simultaneously has, for 10 minutes, a dissolution rate of the proton pump inhibitor in a range of about 10% to about 50% and a dissolution rate of the antacid of about 70% or higher, under dissolution test conditions employing a mixture solution comprising 75 mL of 0.1 N HCl and 225 mL of purified water at about 75±2 revolutions per minute (rpm) at a temperature of 37±0.5° C., according to paddle method of dissolution test of United States Pharmacopeia (USP).

7. The pharmaceutical composite formulation of claim 1, wherein the composite formulation simultaneously has, for 5 minutes, a dissolution rate of the proton pump inhibitor in a range of about 5% to about 30% and a dissolution rate of the antacid of about 60% or higher, under dissolution test conditions employing a mixture solution comprising 75 mL of 0.1 N HCl and 225 mL of purified water at about 75±2 revolutions per minute (rpm) at a temperature of 37±0.5° C., according to paddle method of dissolution test of United States Pharmacopeia (USP).

* * * * *